US00PP22211P3

(12) United States Plant Patent
Bartels

(10) Patent No.: US PP22,211 P3
(45) Date of Patent: Oct. 25, 2011

(54) ***PHLOX* PLANT NAMED 'BARSIXTY'**

(50) Latin Name: *Phlox paniculata*
Varietal Denomination: Barsixty

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 0 days.

(21) Appl. No.: 12/661,586

(22) Filed: Mar. 19, 2010

(65) Prior Publication Data

US 2011/0231975 P1 Sep. 22, 2011

(51) Int. Cl.
*A01H 5/00* (2006.01)

(52) U.S. Cl. ..... Plt./320

(58) Field of Classification Search ..... Plt./320
See application file for complete search history.

*Primary Examiner* — Annette Para
(74) *Attorney, Agent, or Firm* — Jondle & Associates, P.C.

(57) ABSTRACT

A new *Phlox paniculata* plant particularly distinguished by white inflorescences with pink centers and a vigorous growth habit, is disclosed.

2 Drawing Sheets

Genus and species: *Phlox paniculata.*
Variety denomination: 'Barsixty'.

BACKGROUND OF THE NEW PLANT

The present invention comprises a new and distinct cultivar botanically known as *Phlox paniculata,* and hereinafter referred to by the variety name 'Barsixty'. The new variety originated from a crossing made in 2004 in Aalsmeer, The Netherlands. The female parent was the proprietary *Phlox paniculata* plant '01.44.88.01' (unpatented), while the male parent was the proprietary *Phlox paniculata* plant '01.44.95.01' (unpatented).

'Barsixty' was first propagated by vegetative cuttings in 2005 in Aalsmeer, The Netherlands and has been subsequently asexually propagated by vegetative cuttings in Aalsmeer, The Netherlands since 2005. The present invention has been found to retain its distinctive characteristics through successive asexual propagations via vegetative cuttings.

SUMMARY OF THE INVENTION

The following are the most outstanding and distinguishing characteristics of this new variety when grown under normal horticultural practices in Aalsmeer, The Netherlands.

1. White inflorescences with pink center; and
2. A vigorous growth habit.

DESCRIPTION OF THE PHOTOGRAPHS

This *Phlox paniculata* plant is illustrated by the accompanying photographs which show the overall plant habit including blooms, buds, and foliage of the plant; the colors shown are as true as can be reasonably obtained by conventional photographic procedures.

Figure 1:
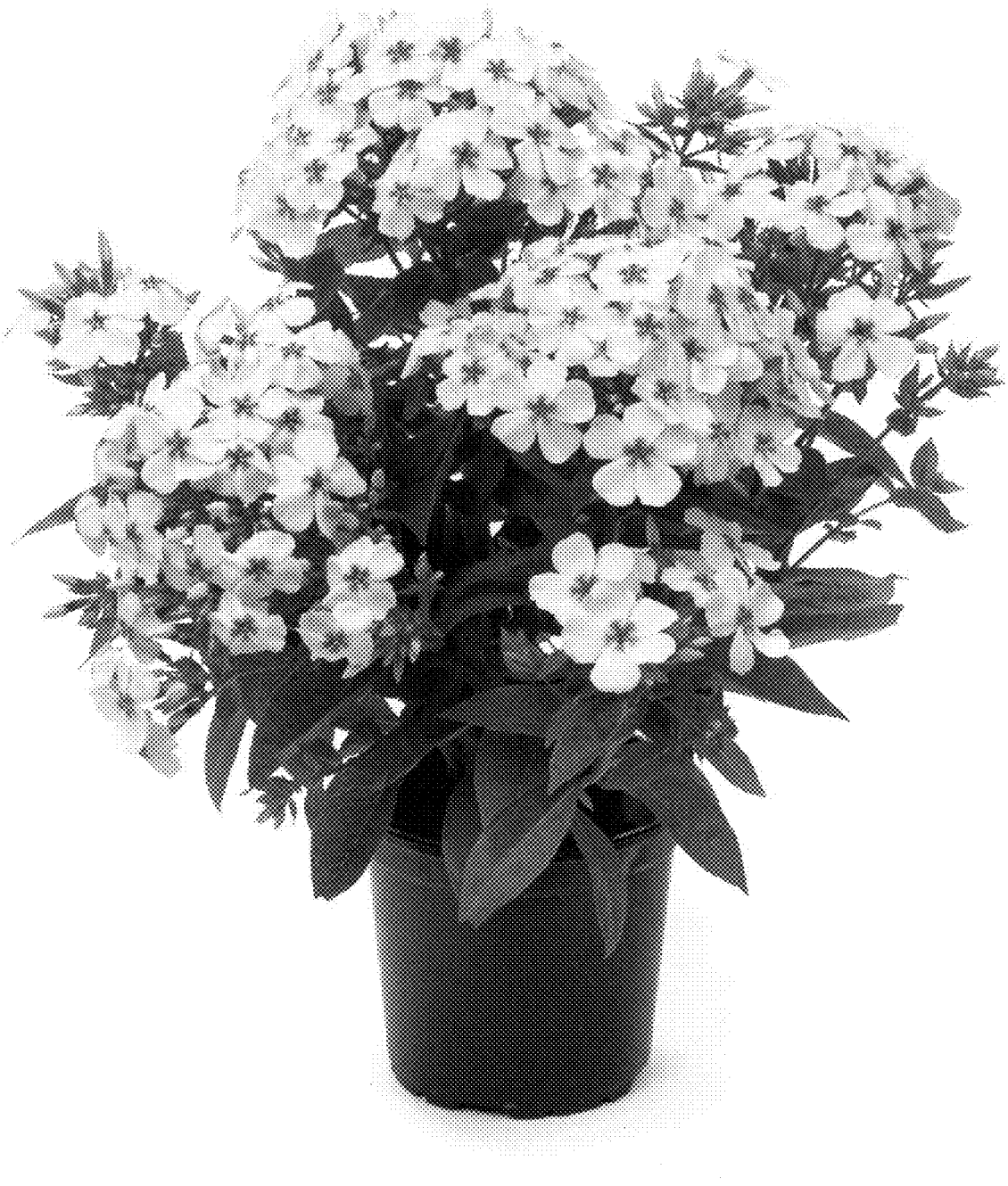
Figure 2:
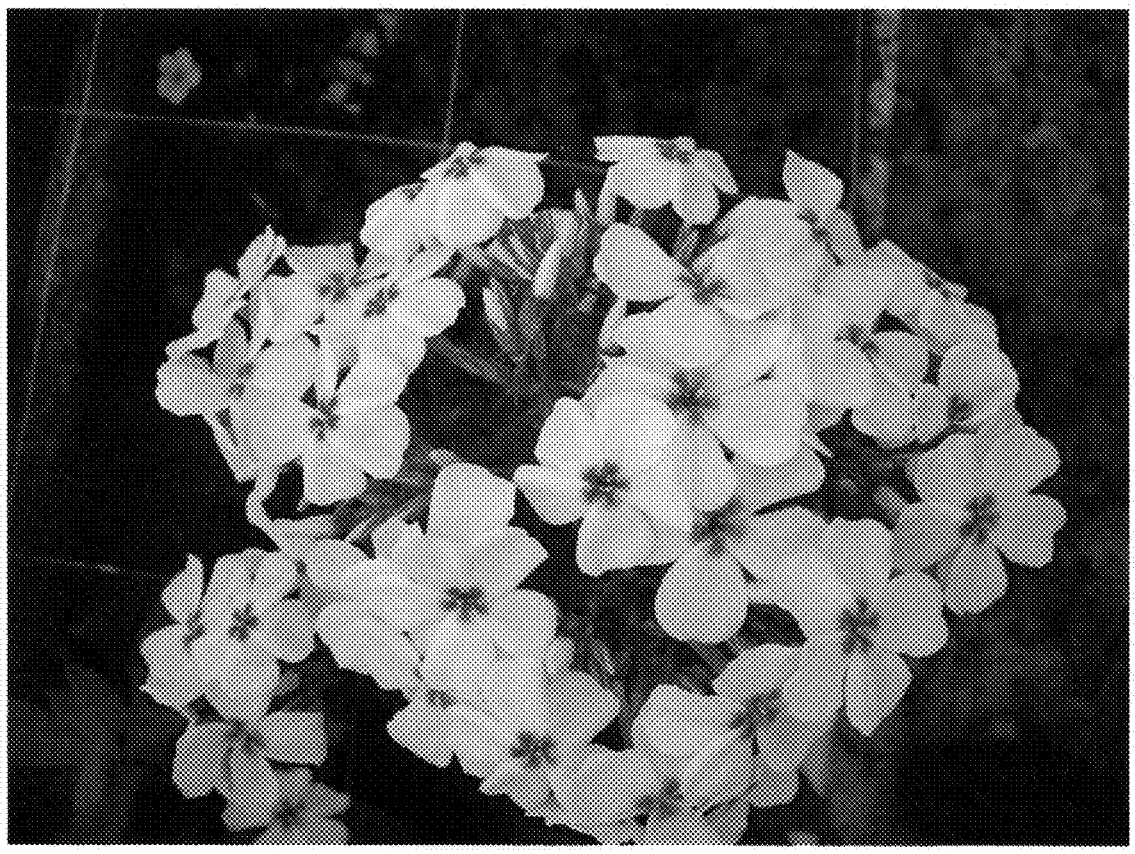

FIG. 1 shows the overall plant habit.
FIG. 2 shows a close-up of the inflorescence.

DESCRIPTION OF THE NEW VARIETY

The following detailed description sets forth the distinctive characteristics of 'Barsixty'. The data which defines these characteristics were collected from asexual reproductions carried out in Aalsmeer, The Netherlands. The plant history was taken on six month old plants that were grown indoors without the use of artificial light and were grown in large crates of six plants each with approximately 50 pounds of peat per crate and with a growing period between May and September. The plants were pinched once at two to three weeks after planting and their stems were harvested regularly. Color readings were taken under natural light outdoors. Color references are primarily to The R.H.S. Colour Chart of The Royal Horticultural Society of London (R.H.S.) (2001).

DETAILED BOTANICAL DESCRIPTION

Classification:
- *Family.*—Polemoniaceae.
- *Botanical name.*—*Phlox paniculata.*
- *Common name.*—Phlox.
- *Denomination.*—'Barsixty'.

Plant:
- *Growth habit.*—Vigorous.
- *Form.*—Narrow, bushy.
- *Height* (*measured from the top of the soil*).—30.0 cm to 40.0 cm.
- *Diameter or area of spread.*—30.0 cm.
- *Propagation.*—Via vegetative cuttings.
- *Time to produce a finished flowering plant.*—4 months.
- *Lastingness of inflorescence on the plant.*—4 weeks.
- *Outdoor plant performance.*—Very good.
- *Time to initiate and develop roots.*—2 weeks.
- *Time to produce rooted cutting or liner* (*young plant*).—5 weeks.

Branches:
- *Number of branches per plant.*—5.
- *Length of lateral branches.*—35.0 cm.
- *Diameter of lateral branches.*—15.0 cm.

Stems:
- *Shape in cross-section.*—Circular.
- *Aspect.*—Smooth.
- *Color.*—RHS 143A.
- *Diameter.*—5.0 to 8.0 mm.
- *Stem length.*—40.0 cm.

*Internode length.*—3.0 to 4.0 cm.
*Anthocyanin.*—Absent.
*Pubescence.*—Absent.

Leaves:
*Color* (*immature and mature leaves*).—Upper surface: RHS 137A. Lower surface: RHS 137A.
*Arrangement.*—Alternate.
*Quantity of leaves* (*per lateral branch*).—26 to 30.
*Apex.*—Accute.
*Base.*—Rounded.
*Margin.*—Smooth.
*Size.*—Length: 8.0 cm. Width: 3.0 cm.
*Shape.*—Lanceolate.
*Pubescence* (*both upper and lower surfaces*).—Absent.
*Venation.*—Type: Feather-like. Color: RHS 144B.
*Texture.*—Smooth.
*Petiole.*—Color: RHS 144B. Length: 3.0 mm. Diameter: 2.0 mm.

Peduncle:
*Length.*—15.0 cm.
*Pubescence.*—Absent.

Inflorescence:
*Inflorescence type.*—Cyme, single flower; self-cleaning.
*Arrangement.*—Terminal and lateral.
*Color.*—RHS 155D and RHS 58B.
*Blooming habit.*—Globe to flattened cyme.
*Height.*—15.0 cm.
*Width.*—15.0 cm.
*Shape.*—Globe to flat shape.
*Fragrance.*—Present.
*Quantity of flowers and buds per plant.*—Greater than 100.

Flowers:
*Flower buds.*—Color: RHS 155B. Shape: Oblong. Size: Length: 3.0 cm. Diameter: 8.0 mm.
*Pedicel.*—Color: RHS 138C. Length: 1.0 cm. Diameter: 0.2 cm. Texture: Smooth.
*Calyx.*—Shape: Funnel. Length: 8.0 mm. Diameter: 3.0 mm.
*Sepals.*—Arrangement: Single whorl. Number: 5. Shape: Narrow triangular. Apex: Pointed. Base: Fused. Margin: Smooth. Size: Length: 6.0 mm. Width: 2.0 mm. Color (mature — both upper and lower surfaces): RHS 138A. Color (immature — both upper and lower surfaces): RHS 138A.
*Corolla.*—Shape: Circular. Color: Inside: RHS 155D and RHS 58B. Outside: RHS 155D. Size: Height (flower depth): 3.0 cm. Diameter: 3.0 cm. Petals: Arrangement: Single whorl. Shape: Rotundate to cuspidate. Number (per flower): 5. Size: Length (from the throat): 1.0 cm. Width: 1.0 cm. Apex: Obcordate. Base: Fused. Margin: Smooth. Color (when opening): Upper surface: RHS 155D. Lower surface: RHS 155D. Color (fully opened): RHS 155D and RHS 58B. Upper surface: RHS 155D. Lower surface: RHS 155D. Color fading to: RHS 155D and RHS 58B. Petal pubescence (both surfaces): Absent.

Reproductive organs:
*Stamens.*—Quantity per flower: 5. Anther: Shape: Linear. Length: 0.2 cm. Anther color: RHS 158A. Pollen color: RHS 158A. Pollen amount: Abundant. Filament: Filament length: 15.0 mm. Filament color: RHS 137B.
*Pistil.*—Quantity: 1. Color: RHS 137B. Size: Length: 20.0 mm. Width: 0.2 mm.
*Style.*—Length: 3.0 cm. Color: RHS 138A.
*Stigma.*—Shape: 3 lobes. Color: RHS 138C.
*Ovary.*—Color: RHS 143A.

Disease resistance: Plant is tolerant to powdery mildew.
Pest resistance: None observed.

COMPARISON WITH COMMERCIAL VARIETY

'Barsixty' differs from the commercial variety 'Bartwentynine' (U.S. Plant Pat. No. 16,259) in that 'Barsixty' has white inflorescences with pink eyes and 4 to 5 stems per plant, while 'Bartwentynine' has white inflorescences with 2 to 3 stems per plant.

I claim:

1. A new and distinct variety of *Phlox paniculata* plant as described and shown herein.

* * * * *